United States Patent
Eicher et al.

(10) Patent No.: US 7,629,495 B2
(45) Date of Patent: Dec. 8, 2009

(54) PROCESS FOR THE MANUFACTURE OF 1,1,1,3,3-PENTAFLUOROPROPANE

(75) Inventors: Johannes Eicher, Sehnde (DE); Stefan Mross, Brussels (BE)

(73) Assignee: Solvay (Société Anonyme), Brussels (BE)

( * ) Notice: Subject to any disclaimer, the term of this patent is extended or adjusted under 35 U.S.C. 154(b) by 0 days.

(21) Appl. No.: 12/282,556

(22) PCT Filed: Mar. 22, 2007

(86) PCT No.: PCT/EP2007/052771

§ 371 (c)(1),
(2), (4) Date: Sep. 11, 2008

(87) PCT Pub. No.: WO2007/110379

PCT Pub. Date: Oct. 4, 2007

(65) Prior Publication Data

US 2009/0062576 A1    Mar. 5, 2009

(30) Foreign Application Priority Data

Mar. 24, 2006 (EP) .................................. 06111712

(51) Int. Cl.
  *C07C 17/08* (2006.01)
(52) U.S. Cl. ...................... 570/164; 570/134
(58) Field of Classification Search .................. 570/164
  See application file for complete search history.

(56) References Cited

U.S. PATENT DOCUMENTS

| | | | | |
|---|---|---|---|---|
| 5,545,772 A | * | 8/1996 | Pennetreau et al. | 570/164 |
| 5,777,185 A | * | 7/1998 | Belter | 570/164 |
| 5,847,245 A | * | 12/1998 | Franz et al. | 570/175 |
| 5,969,199 A | * | 10/1999 | Franz et al. | 570/175 |
| 6,111,150 A | | 8/2000 | Sakyu et al. | |
| 6,362,382 B1 | * | 3/2002 | Chen et al. | 570/164 |
| 2006/0041174 A1 | * | 2/2006 | Piepho et al. | 570/101 |

FOREIGN PATENT DOCUMENTS

| | | |
|---|---|---|
| EP | 0522639 A1 | 1/1993 |
| EP | 0877009 A1 | 11/1998 |
| EP | 1067106 A1 | 1/2001 |
| JP | 2004043410 A | 2/2004 |

OTHER PUBLICATIONS

G. Aranda, "Obtention de fluoroalcools arylaliphatiques par la voie des epoxydes et des fluorhydrates d'amines [Preparation of araliphatic fluoro alcohols from epoxides and amine hydrofluorides]", Bulletin de la Societe Chimique de France, 1965, vol. 6, pp. 1890-1892; included CAS abstract in English (4 pp.).

R. Franz, "Ueber trishydrofluoride tertiaerer amine und ihren einsatz als fluorierungsmittel [Tertiary Amine tris (hydroflurides) and their use as fluorinating agents]", Journal of Fluorine Chemistry, 1980, pp. 423-434, vol. 15, Elsevier Sequoia S.A, Lausanne - Printed in Netherlands; included CAS abstract in English (13 pp.).

* cited by examiner

*Primary Examiner*—Brian J Davis
(74) *Attorney, Agent, or Firm*—Beatrice C. Ortego

(57) ABSTRACT

A process for the manufacture of 1,1,1,3,3-pentafluoropropane which comprises adding hydrogen fluoride to 1,1,1,3-tetrafluoropropene in the substantial absence of metal catalyst. Another embodiment provides for the manufacture of 1,1,1,3,3-pentafluoropropane which comprises adding hydrogen fluoride to 1,1,1,3-tetrafluoropropene in the presence of an amine hydrofluoride complex and a metal catalyst.

18 Claims, No Drawings

PROCESS FOR THE MANUFACTURE OF 1,1,1,3,3-PENTAFLUOROPROPANE

CROSS-REFERENCE TO RELATED APPLICATIONS

This application is a U.S. national stage application under 35 U.S.C. §371 of International Application No. PCT/EP2007/052771, flied Mar.22, 2007, which claims priority to European Application No. EP06111712.3, filed Mar. 24, 2006, all of these applications being herein incorporated by reference in their entirety for all purposes.

The present invention relates to a process for the manufacture of 1,1,1,3,3-pentafluoropropane. 1,1,1,3,3-pentafluoropropane is useful amongst others as constituent of blowing agents for polyurethane foams in compositions with 1,1,1,3,3-pentafluorobutane.

The invention allows for efficient manufacture of 1,1,1,3,3-pentafluoropropane.

The invention concerns, in one embodiment, a process for the manufacture of 1,1,1,3,3-pentafluoropropane which comprises adding hydrogen fluoride to 1,1,1,3-tetrafluoropropene in the substantial absence of metal catalyst.

The meaning of "substantial absence of metal catalyst" is clear to the expert skilled in the art. For example, the term does not exclude the presence or the addition of trace amounts of metals or metal compounds, or the presence or addition of metals or metal compounds in amounts which do not accelerate the reaction speed by more than 5%, preferably by more than 2%. especially in the temperature range of −10° C. to 200° C. For example, the term also does not exclude the presence of unwanted impurities, for example, impurities contained in the starting material introduced into the reaction mixture, or impurities which entered the reaction mixture as result of corrosion, for example, of the reactor, lines or other equipment. Preferably, no metal catalyst is added to the reaction mixture.

Said addition is generally carried out under conditions sufficient to maximize production of 1,1,1,3,3-pentafluoropropane. Certain methods for providing starting material 1,1,1,3-tetrafluoropropene are known e.g. from JP 2004-043410-A.

The process according to the invention therefore suitably further comprises a step wherein 1,1,1,3-tetrafluoropropene is produced by fluorination of a chloro(fluoro) compound. The chloro(fluoro)compound is preferably 1-chloro-3,3,3-trifluoropropene. The 1-chloro-3,3,3-trifluoropropene can be obtained by hydrofluorination of 1,1,1,3,3-pentachloropropane, in one embodiment, that reaction is carried out in the absence of fluorination catalyst.

The reaction temperatures which can be used in the process according to the invention are in general equal to or higher than about −10° C. preferably equal to or higher than about 0° C., particularly preferably equal to or higher than about 20° C. or equal to or higher than about 50° C. The reaction temperatures which can be used in the process according to the invention are in general equal to or lower than about 200° C., preferably equal to or lower than about 100° C. and particularly preferably equal to or lower than about 80° C. For certain embodiments, the reaction temperature can be even higher than 200° C. For example, it can be as high as 400° C.

The process according to the invention can be carried out in a closed pressure vessel or at atmospheric pressure. If the reaction is carried out batchwise, a stirred autoclave is expediently selected in which the reaction can proceed under autogenous pressure. In this case, the progress of the reaction is as a rule recognizable by the decrease in the internal pressure. A stirred flask, optionally with a reflux condenser, can also be used. After the end of the reaction the amount of HF consumed can be replaced again in a suitable manner, e.g. by passing in, condensing in or pumping in HF, and a further reaction can follow.

The reaction can also suitably be carried out continuously.

The reaction is preferably carried out in a liquid phase, more preferably a homogeneous liquid phase.

If it is intended to carry out a liquid phase reaction without pressure, the residence time of the substrate needed for reaction can be realized by means of a gas circulation. The addition of the HF can in this case also be carried out simultaneously with the addition of the substrate. In this case, it is preferred to carry out the process continuously in a bubble column which can consist of corrosion-resistant metal, borosilicate glass or synthetic material.

In general, addition of solvent is unnecessary; if required, however, the reaction can be carried out in the presence of adequate amounts of an aprotic polar solvent such as dioxane, tetrahydrofuran, acetonitrile or N-methylpyrrolidone.

The hydrofluorination product can be isolated for example by distillation or (when using a pressure vessel) by releasing the pressure and condensing. It is a particular advantage of the process according to the invention that the hydrofluorination products thus prepared are free of impurities whose formation interferes in other preparation processes which proceed at high temperatures.

In a specific aspect, the reaction can be carried out in the presence of an activator for HF other than metal catalysts.

In a particular aspect, the invention concerns a process for the manufacture of 1,1,1,3,3-pentafluoropropane which comprises adding hydrogen fluoride to 1,1,1,3-tetrafluoropropene by contacting said 1,1,1,3-tetrafluoropropene with an amine hydrofluoride complex. The general description of the invention given here before applies in particular to this particular aspect.

The amine hydrofluoride complex is preferably at least one hydrofluoride of an organic nitrogen base of the formula (I)

[B*n HF]    (I)

in which B is an organic nitrogen base and n is an integer or fraction less than or equal to 4.

Suitable nitrogen bases B of the formula (I) are amines including nitrogen heterocycles. When the formula given for these amines is the formula (II)

$R^4R^5R^6N$    (II), the radicals $R^4$, $R^5$ and $R^6$ therein can be identical or different and are hydrogen, an alkyl radical having 1 to 20, preferably having 1 to 12, in particular having 1 to 6 carbon atoms, an alkenyl radical having 2 to 20, preferably 2 to 12, in particular 2 to 6 carbon atoms, a cycloalkyl radical having 5 to 7 carbon atoms, a cycloalkenyl radical having 5 to 7 carbon atoms, an aralkyl radical having 7 to 10 carbon atoms or an aryl radical having 6 to 10 carbon atoms which can additionally be substituted by $C_1$-$C_3$-alkyl or $C_2$-$C_3$-alkoxy groups.

The alkyl, cycloalkyl, aralkyl and aryl radicals mentioned are preferred here.

In addition, two of the radicals $R^4$ to $R^5$, together with the nitrogen atom carrying them, can form a 5- to 7-membered ring which can contain an oxygen atom or a further nitrogen atom, preferably, however, such a ring contains no oxygen atom and no further nitrogen atom. This ring thus has 5 to 7 members, of which one is the nitrogen atom and the others are preferably CH₂ groups. One of the CH₂ groups can also be replaced by an oxygen or nitrogen atom, which, however, is not preferred.

Together with the nitrogen atom carrying them, the radicals R⁴ to R⁶ can also form two or three 5- to 7-membered, preferably saturated, rings which can contain further nitrogen atoms, such as, for example, in hexamethylenetetramine or diazabicyclooctane.

The nitrogen base B can additionally be a 6-membered heterocyclic ring which can contain one or two nitrogen atoms and can also be benzo-fused, e.g. pyridine, pyrimidine or quinoline.

Particularly preferred organic nitrogen bases B are tertiary amines, including N-heterocycles, having a total of 3 to 12 carbon atoms, especially the following: tri-methylamine, tri-ethylamine, tri-n-propylamine, isopropyl-diethylamine, tri-n-butylamine, N,N,-dimethylaniline, N-methylpiperidine, pyridine, quinoline, N,N'-tetra-methylethylenediamine and hexamethylenetetramine.

The number n in the formula (I) is the molar amount of HF per nitrogen atom of the base B and is an integer or fraction less than or equal to 4, preferably 0.5 to 3.5, in particular 2 to 3.

In the following, examples of the complex hydrofluorides of the formula (II) which can be employed in the process according to the invention are given:

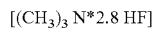

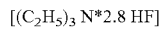

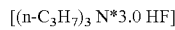

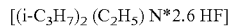

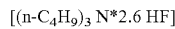

These hydrofluorides are known from the literature, e.g. from Bulletin Soc. Chim. France 1965, pages 1890 to 1892 or from J. Fluorine Chemistry 15 (1980), pages 423 to 434. in the molar composition given, they are stable complexes which, in contrast to amine hydrofluorides having a higher hydrogen fluoride content (n>4), such as e.g. [pyridine*9 HF], i.e. "Olah's reagent", exhibit no HF vapor pressure and are therefore considerably simpler to handle and in some cases can even be distilled in equipment made of borosilicate glass. In the process according to the invention, the use of [triethylamine*2.8 HF] or [tributylamine*2.6 HF] is particularly preferred.

Another embodiment of the present invention concerns a process for the manufacture of 1,1,1,3,3-pentafluoropropane which comprises adding hydrogen fluoride to 1,1,1,3-tetrafluoropropene by contacting said 1,1,1,3-tetrafluoropropene with an amine hydrofluoride complex in the presence of a metal catalyst. The amine hydrofluoride complex and its preferred features which can also be applied in this embodiment are described above. The metal catalyst is preferably a metal or a metal compound which is known to promote the formation of 1,1,1,3,3-pentafluoropropane from 1,1,1,3-tetrafluoropropene in the presence of HF. For example, among the suitable catalysts which can be applied in this embodiment together with the amine hydrofluoride complex, the metal compounds can be cited which are described in EP-A 522 639. According to that application, metal compounds of metals of the groups IIIa, IVa and IVb, Va and Vb and VIb of the periodic table and mixtures of such metal compounds can be applied. Preferably, compounds of titanium, tantalum, molybdenum, boron, tin and antimony, and especially preferably, compounds of tin and antimony, are applied. As compounds, the salts of the metals are mentioned, especially the halides. Preferred halides are the chlorides, the fluorides and chlorofluorides. Especially preferred metal catalysts to be applied together with amine hydrofluoride complexes in this embodiment of the present invention are the chlorides, fluorides or chlorofluorides of antimony and tin and mixtures thereof. It is often advantageous to add metal chlorides as metal catalyst. The molar ratio of amine hydrofluoride complex to metal catalyst preferably lies in a range of 1:100 to 100:1. Amine hydrofluoride and metal catalyst can be applied simultaneously during at least a part of the reaction time in reactions performed batchwise.

In a particular embodiment, the process according to the invention is carried out with hydrogen fluoride in the substantial absence of other fluorination reagents or catalyst. In this embodiment, the addition of hydrogen fluoride to 1,1,1,3-tetrafluoropropene can advantageously be promoted thermally. In this case, the reaction is typically carried out at a temperature of from 50 to 400° C., preferably from 60 to 350° C. In this aspect, the reaction can be carried out in liquid or gas phase, preferably in the gas phase. If carried out in the liquid phase, the reaction temperature is preferably in the lower range, e.g. in the range from 50 to 150° C. Here, a preferred temperature range is 60 to 120° C. If carried out in the gas phase, the reaction is preferably performed in the upper range, for example in the range from 100 to 400° C. A preferred temperature range is 100 to 350° C., still more preferably 150 to 300° C.

The following examples illustrate the process according to the invention in a non limitative manner.

EXAMPLE 1

1900 g (8.0 mol) of [(n-C₄H₉)₃ N*2.6 HF] are introduced into a 5 liter stirred autoclave and 452 g of 1,1,1,3-tetrafluoropropene (4.0 mol) are pumped in from a storage reservoir with stirring at 20° C. The autoclave is then heated to 75° C. and after reaching this temperature the pressure is released through a trap cooled with dry ice. The contents of this trap (610 g) consist essentially of 1,1,1,3,3-pentafluoropropane.

The invention claimed is:

1. A process for the manufacture of 1,1,1,3,3-pentafluoropropane which comprises adding hydrogen fluoride to 1,1,1,3-tetrafluoropropene in the substantial absence of metal catalyst.

2. A process for the manufacture of 1,1,1,3,3-pentafluoropropane which comprises adding hydrogen fluoride to 1,1,1,3-tetrafluoropropene in the presence of an amine hydrofluoride complex.

3. The process according to claim 2, wherein the amine hydrofluoride complex is at least one hydrofluoride of an organic nitrogen base of the formula (I)

in which B is an organic nitrogen base and n is an integer or fraction less than or equal to 4.

4. The process according to claim 1, wherein the reaction is carried out at a temperature from −10 to 200° C.

5. The process according to claim 4, wherein the reaction is carried out at a temperature from 50 to 80° C.

6. The process according claim 1, wherein the reaction is carried out in a liquid phase.

7. The process according to claim 1, wherein the reaction is carried out continuously.

8. The process according claim 1, which further comprises a step wherein 1,1,1,3-tetrafluoropropene is produced by fluorination of a chloro(fluoro) compound.

9. The process according to claim 8, wherein the chloro(fluoro)compound is 1-chloro-3,3,3-trifluoropropene.

10. The process according to claim 9, wherein the 1-chloro-3,3,3-trifluoropropene is obtained by hydrofluorination of 1,1,1,3,3-pentachloropropane in the absence of fluorination catalyst.

11. A process for the manufacture of 1,1,1,3,3-pentafluoropropane which comprises adding hydrogen fluoride to 1,1,1,3-tetrafluoropropene in the presence of an amine hydrofluoride complex and a metal complex.

12. The process according to claim 2, wherein the reaction is carried out at a temperature from −10 to 200° C.

13. The process according to claim 11, wherein the reaction is carried out at a temperature from 50 to 80° C.

14. The process according to claim 2, wherein the reaction is carried out in a liquid phase.

15. The process according to claim 2, wherein the reaction is carried out continuously.

16. The process according to claim 2, further comprising a step wherein 1,1,1,3-tetrafluoropropene is produced by fluorination of a chloro(fluoro) compound.

17. The process according to claim 15, wherein the chloro(fluoro)compound is 1-chloro-3,3,3-trifluoropropene.

18. The process according to claim 16, wherein the 1-chloro-3,3,3-trifluoropropene is obtained by hydrofluorination of 1,1,1,3,3-pentachloropropane in the absence of fluorination catalyst.

\* \* \* \* \*